(12) United States Patent
Augsburger et al.

(10) Patent No.: US 8,110,223 B2
(45) Date of Patent: Feb. 7, 2012

(54) METHODS FOR MAKING PHARMACEUTICAL DOSAGE FORMS CONTAINING ACTIVE CUSHIONING COMPONENTS

(75) Inventors: Larry Augsburger, Severna Park, MD (US); Ngoc Do, Bel Air, MD (US); Min Michael He, Ellicott City, MD (US); Cheng Der Tony Yu, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 1337 days.

(21) Appl. No.: 10/749,339

(22) Filed: Dec. 31, 2003

(65) Prior Publication Data

US 2005/0019393 A1 Jan. 27, 2005

Related U.S. Application Data

(63) Continuation-in-part of application No. 10/633,445, filed on Aug. 1, 2003, now abandoned, and a continuation-in-part of application No. 10/444,621, filed on May 23, 2003, now abandoned.

(60) Provisional application No. 60/437,507, filed on Dec. 31, 2002.

(51) Int. Cl.
*A61K 9/14* (2006.01)
*A61K 9/50* (2006.01)
(52) U.S. Cl. ......... 424/489; 424/490; 424/494; 424/498
(58) Field of Classification Search .................. None
See application file for complete search history.

(56) References Cited

U.S. PATENT DOCUMENTS

| 4,910,023 A * | 3/1990 | Botzolakis et al. ........... 424/470 |
| 5,223,264 A | 6/1993 | Wehling et al. |
| 5,639,475 A | 6/1997 | Bettman et al. |
| 5,780,055 A * | 7/1998 | Habib et al. .................. 424/464 |
| 5,807,577 A | 9/1998 | Ouali |
| 6,126,967 A * | 10/2000 | Clemente et al. ............. 424/461 |
| 6,221,392 B1 | 4/2001 | Khankari et al. |
| 6,254,891 B1 * | 7/2001 | Anaebonam et al. ......... 424/497 |
| 6,340,476 B1 | 1/2002 | Midha et al. |

FOREIGN PATENT DOCUMENTS

EP 0 196 546 1/1992

OTHER PUBLICATIONS

Mesh to Micron Conversion Chart, downloaded from the world wide web on Jul. 11, 2007.*
Aulton et al., 1994, "The strength and compaction of millispheres: The design of a controlled-release drug delivery system for ibuprofen in the form of a tablet comprising compacted polymer-coated millispheres," Drug Dev. and Indust. Pharm., 20(20):3069-3104.
Mount et al., 1996, "Formulation and compaction of nonfracturing deformable coated beads," Drug Dev. and Indust. Pharm., 22(7):609-621.
O'Connor et al., 2000, "Powders," in *Remington: The Science and Practice of Pharmacy* (Gennaro A.R., 20th ed.), ch. 37, pp. 681-685.
Rudnic et al., 2000, "Oral solid dosage forms," in *Remington: The Science and Practice of Pharmacy* (Gennaro A.R., 20th ed.), ch. 45, pp. 858-902.
Sprowls, Jr., 1960, "Wafers, cachets, konseals," in *American Pharmacy*, pp. 425-426.
International Search Report, of International Application PCT/US03/41765, dated May 7, 2004.
International Preliminary Examination Report, of International Application PCT/US03/41765, dated Oct. 1, 2004.

* cited by examiner

*Primary Examiner* — Michael G Hartley
*Assistant Examiner* — Micah-Paul Young
(74) *Attorney, Agent, or Firm* — Nevrivy Patent Law Group P.L.L.C.

(57) ABSTRACT

Novel methods for making dosages form comprising a cushioning component. The methods of the present invention provides dosage forms which can be compressed to form compressed dosage forms that are substantially uniform in composition and robust and exhibit reduced friability. The invention also relates to methods for making fast-disintegrating dosage forms.

11 Claims, 3 Drawing Sheets

SR-Active Bead

Cushioning Bead

Co-Processed Active-Cushioning Bead

Cushioning Layer

SR-Coating Layer

Drug Loading Layer

Drug Loading Layer & Inert Nonpareil Seed can be substituted with a Drug-Loading Matrix Inert Nonpareil Seed Cross-sectional Diagram of Co-processed Active-Cushioning Beads

METHODS FOR MAKING PHARMACEUTICAL DOSAGE FORMS CONTAINING ACTIVE CUSHIONING COMPONENTS

This application claims the benefit of U.S. Provisional Application No. 60/437,507, filed Dec. 31, 2002, and is a continuation-in-part of U.S. application Ser. No. 10/633,445, filed Aug. 1, 2003 now abandoned and a continuation-in-part of U.S. application Ser. No. 10/444,621, filed May 23, 2003, now abandoned both of which claim the benefit of U.S. Provisional Application No. 60/437,507, filed Dec. 31, 2002, the entire disclosure of each of the aforementioned applications being incorporated by reference herein in its entirety.

1. FIELD OF THE INVENTION

The invention relates, to methods for making dosage forms comprising active cushioning components and methods for administering the dosage forms to a patient in need thereof. The invention also relates to methods for making fast-disintegrating dosage forms comprising active cushioning components.

2. BACKGROUND

There has been developing interest in using solid dosage forms for administration of pharmaceutically active agents. The majority of solid dosage forms, such as tablets and capsules, are intended for oral administration. Upon ingestion, the tablet disintegrates, the contents of the tablets disperse, and medicament(s) are released in the gastrointestinal ("GI") tract. The release of the medicaments of the tablets could be rapid or immediate; the release could be delayed for some period after ingestion; or the release could occur in a controlled or sustained manner. Compared to other dosage forms such as suspensions, solutions, or elixers, tablets and capsules tend to have increased robustness, increased stability, and certain manufacturing advantages such as low cost of manufacturing, packaging, and shipping.

Yet, in spite of the advantages of tablet dosage forms, certain limitations still exist. For instance, limitations of tablet dosage forms become evident when tablets are compressed during preparation of the dosage form. The robustness of a compressed tablet can generally be increased by compressing the tablet components with increasing force. However, increasing the tablet compression force tends to adversely affect tablet disintegration properties. Another limitation of the tablets is the breakage of the sustained release or enteric coatings of the active beads or granules during compression.

Capsules are often used to contain beads with sustained release or enteric coatings to avoid these limitation of traditional tablets. However, capsules also have limitations, including loss of aqueous solubility of gelatin capsules due to cross-linking, particularly upon exposure to trace quantities of active aldehydes; gelatin capsules must be protected from extremes of humidity to preserves the desired mechanical properties; capsule filling machines are slower than typical production tablet presses; capsules are most susceptible to tampering; and gelatin capsules are made from animal sources which may be unacceptable to some patient populations for dietary or religious reasons.

There exists a need for tablets with components with sustained release or enteric coatings capable of withstanding breakage during compression.

There have been numerous efforts to overcome the limitations experienced during compression of tablet dosage forms. For example, EP 0 196 546 B1 alleges that the fracture of coated active-containing granules occurring during tablet compression is reduced by including microcrystalline cellulose in the tablet matrix. U.S. Pat. No. 5,780,055 to Habib et al. allegedly provides a method for preparing a crushed tablet comprising compressing active-loaded particles with highly porous freeze-dried cushioning beads. Such cushioning beads are spherical or semi-spherical agglomerates of suitable composition having structural and deformation properties suitable for forming a compressible composition when admixed with suitable proportions of membrane coated active-loaded particles. The reference discloses that the cushioning beads deform preferentially, i.e., they deform at lower pressures than the membrane-coated active beads, to substantially prevent rupture or cracking of the membrane of the active-loaded particles. Generally, cushioning beads, including those described in Habib, do not contain a biologically active substance and are referred to as "placebo millispheres" (see Aulton et al. in 20 *Drug Development and Industrial Pharmacy* 3094 (1994)) and "cushioning agents" (see Mount et al. in 22 *Drug Development and Industrial Pharmacy* 612 (1996)).

However, the highly porous cushioning beads are lighter in weight than the active-loaded particles, by virtue of its functionality. The incorporation of these two types of beads with drastically different densities into a tablet presents several problems. First, segregation of the heavier beads from the lighter beads in the hopper is inevitable. Secondly, the homogeneity of the powder blend can not be assured during transport. Thirdly, the unevenly distributed cushioning beads defeats their purpose of protecting the active-loaded particles during compression. As a result, the dose uniformity of the tablets and the integrity of the coatings of the beads become questionable.

There is a need to develop methods for preparing tablet dosage forms incorporating cushioning components which allow greater compressibility of the table components yet overcome the problems presented by incorporating cushioning components with the active pharmaceutical components. In particular, there is a need for methods of preparing tablets such that dose uniformity and integrity of coatings useful for achieving certain release profiles is maintained.

Another limitation of tablets arises from the need to incorporate a large quantity of biologically active ingredient(s) into a tablet can often result in tablets of such a large size that administration is unsuitable for geriatric and pediatric patients, or certain patients who already have difficulty in swallowing solid medications. Oral solutions such as liquid suspension dosage forms have been developed as an alternative to tablets in order to circumvent this problem; however, many challenges are encountered by a pharmaceutical scientist in the development of a suspension. Suspensions are often thermodynamically unstable and may result in aggregation and sedimentation during storage. Problems are often encountered because the accuracy of the dose depends on the even distribution of particles in the suspensions at the time the preparations are administered to the patients.

Accordingly, it is often desirable to have a tablet that disintegrates and disperses rapidly in the mouth without requiring any water intake other than the normal flow of saliva. Such tablets are easier for the elderly and children who often have difficulty in chewing or swallowing large capsules or tablets; they are convenient to use since the patient may not have convenient access to water for swallowing conventional dosage forms; and they may be particularly convenient dosage forms for delivering larger drug doses for any patient, because fast-disperse tablets are never swallowed whole. Thus, even large doses of drug that would otherwise require excessively large single tablets or capsules or the administration of multiple tablets or capsules at one time may be conveniently administered in a single rapid-disperse tablet that does not need to be swallowed whole. This overcomes one of the limitations of tablets containing a large quantity of biologically active ingredient(s), where the resulting large size tablets are often unsuitable for administration to geriatric and pediatric patients, or certain patients who have difficulty in swallowing solid medications.

Accordingly, there remains a need to formulate a rapidly disintegrating tablet which disperses in a liquid to form a ready-to-use suspension in order to overcome a number of the challenges by combining the advantages of both tablets and suspensions and circumventing their shortcomings.

U.S. Pat. No. 6,221,392 to Khankari et al. discloses a fast-dissolving tablet utilizing a rapidly dissolvable filler and a relatively high level of lubricant.

U.S. Pat. No. 5,223,264 Wehling et al., U.S. Pat. No. 5,639,475 to Bettman et al. and U.S. Pat. No. 5,807,577 to Ouali disclose fast-disintegrating tablets utilizing an effervescent material to promote disintegration.

A rapid-disintegration tablet should be palatable to the patient. When necessary, palatability of drugs can generally be enhanced through the application of existing technologies; for example, those that involve coating and/or microencapsulation or formulation means. Additionally, the rapid-disintegration tablet must have adequate hardness and resistance to resist chipping and abrasion during manufacture, packaging and handling without unduly increasing the disintegration time upon administration to a patient.

There is a need for a highly compactable, rapidly dispersing tablet matrix containing one or more pharmaceutically active compounds that may be directly compressed to form rapidly dispersing tablets with practical hardness and resistance to chipping and abrasion. The primary challenge in developing tablets capable of rapid dispersion is the achievement of palatability and adequate robustness without compromising disintegration times. As such, there is a need for tablets that overcome such a challenge.

There also is a need to design a rapidly disintegrating tablet not only for an immediate release pattern but also for a modified-release model and others. Protective functional coatings, i.e., enteric or sustained-release coating, are usually intended to release the biologically active ingredient(s) at a certain part of the gastrointestinal (GI) tract or over a longer period of time after administration. In the case where active-loaded and membrane-coated beads or pellets are to be compressed into tablets, it is critical that the integrity of the functional coatings are maintained during compression.

Accordingly, there is a need for tablets that comprise very small cushioning components, which are particularly useful in the manufacture of dosage forms such as fast-disintegrating tablets which must be capable of being compressed yet retain disintegration rates and dose uniformity and robustness.

In sum, there is an overall need in the art for greater understanding of more efficient methods for preparing and utilizing solid dosage forms which comprise cushioning components which allow for compression of a tablet dosage form using conventional manufacturing equipment.

Citation of any reference in Section 2 of this application is not an admission that the reference is prior art to the application.

3. SUMMARY OF THE INVENTION

The present invention is based in part on the surprising discovery that uniformity and non-segregation can be achieved by co-processing cushioning components with active pharmaceutical ingredients during the formulation of compressible tablet dosage forms. In particular, the inventors have demonstrated that co-processing the various components together unexpectedly allows for the use of conventional manufacturing equipment during large scale manufacturing of a compressible tablet dosage form.

The present invention is also based in part on the further surprising discovery that the advantages of incorporating cushioning components with active pharmaceutical ingredients during the manufacturing process can be retained even after milling of the tablet components in order to achieve a tablet capable of rapid dispersion. In particular, the inventors have accomplished the manufacture of pharmaceutical dosage forms comprised of a highly compactable, rapidly dispersing tablet matrix that incorporates one or more pharmaceutically active ingredients and retains the advantages imparted by the presence of a cushioning component.

As such, the present invention relates to novel methods for making dosage forms comprising an active cushioning component. The methods of the present invention provide compressible dosage forms which can be compressed to form tablet dosage forms which are substantially uniform in composition and robust.

In one embodiment, the present invention relates to a compressible dosage form comprising an active cushioning component, wherein the active cushioning component comprises an active agent, a highly-compactable filler and a highly water-absorbing material.

In another embodiment, the present invention relates to a compressible dosage form comprising an active cushioning component, wherein the active cushioning component comprises:

(a) a placebo cushioning component comprising a highly-compactable filler, a highly water-absorbing material and water; and (b) active-loaded particles; wherein the placebo cushioning component and active-loaded particles are admixed to form an admixture; and the admixture is freeze-dried to form the active cushioning component.

In another embodiment, the present invention relates to a compressible dosage form comprising an active cushioning component, wherein the active cushioning component comprises:

(a) freeze-dried placebo cushioning component comprising a highly-compactable filler and a highly water-absorbing material, and having a particle size ranging from about 20 μm up to about 2000 μm; and (b) active-loaded particles; wherein the freeze-dried placebo cushioning component and active-loaded particles are admixed to form the active cushioning component.

The invention also relates to methods for preparing pharmaceutical dosage forms comprising active cushioning components of the invention.

In one embodiment, the present invention relates to methods for preparing a compressible dosage form comprising an active cushioning component, comprising:

(a) combining a highly-compactable filler, a highly water-absorbing material and water to form a placebo cushioning component;

(b) providing active-loaded particles;

(c) admixing the placebo cushioning component and active-loaded particles to form an admixture; and (d) freeze-drying the admixture to form the active cushioning component.

In another embodiment, the present invention relates to methods for preparing a compressible dosage form comprising an active cushioning component, comprising:

(a) combining a highly-compactable filler, a highly water-absorbing material and water to form a placebo cushioning component;

(b) freeze-drying the placebo cushioning component to form a freeze-dried placebo cushioning component;

(c) milling the freeze-dried placebo cushioning component to form a freeze-dried placebo cushioning component having a particle size ranging from about 45 µm up to about 2000 µm;

(d) providing active-loaded particles; and (e) admixing the freeze-dried placebo cushioning component having a particle size ranging from about 20 µm up to about 2000 µm and the active-loaded particles to form the active cushioning component.

The invention still further relates to methods for preparing rapidly-disintegrating dosage forms comprising active cushioning components of the invention. In alternate embodiments, the dosage forms comprise placebo cushioning components and active components which are milled to a very small size, capable of being compressed into tablets or lozenges which have rapid disintegration rates.

The present invention can be understood more fully by reference to the following detailed FIGS., description and illustrative examples, which exemplify non-limiting embodiments of the invention.

4. BRIEF DESCRIPTION OF THE DRAWINGS

Figure 3:
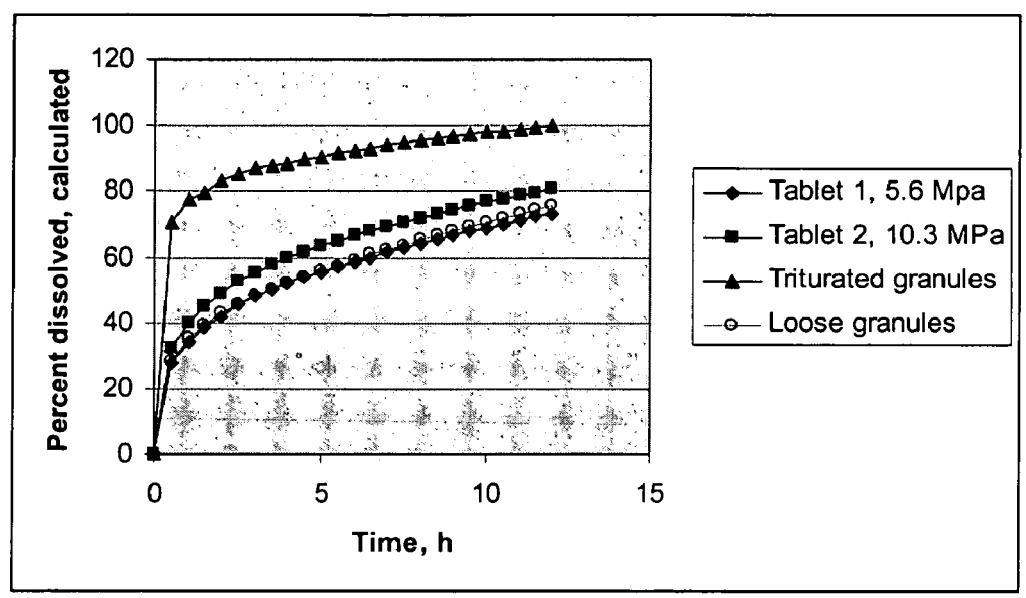

FIG. 3 shows the amount of active ingredient dissolved when tablets comprising a granular freeze-dried admixture comprising (a) prednisolone sodium phosphate-loaded beads coated with a sustained-release coating and (b) a placebo cushioning component were compressed with a force of 5.6 mPa (Tablet 1, -♦-) or 10.3 mPa (Tablet 2, -■-) were placed 0.1 N HCl at 37° C. The data reported are normalized to a triturated form of the above granular freeze-dried admixture (-▲-). FIG. 3 also includes dissolution data for a loose granular freeze-dried admixture data granules (-○-) normalized to the triturated form of the above granular freeze-dried admixture.

5. DETAILED DESCRIPTION OF THE INVENTION

As described above, the present invention encompasses methods for manufacturing tablet dosage forms which overcome the segregation and dosage uniformity problems posed during the manufacture of dosage forms comprising cushioning components. The methods involve co-processing multiple components, in particular, active and cushioning components, into an active cushioning component which is capable of being compressed into a tablet dosage form. Such dosage forms have a uniform distribution of active components throughout the cushioning components. During transportation and storage, the multiple components are prevented from segregating, thereby insuring dosage uniformity of the resulting tablets.

5.1 Definitions

As used herein, the phrase "active cushioning component" can encompass a bead, particle or granule comprising an active agent and a placebo cushioning component comprising a highly-compactable filler and a highly water-absorbing material; and the placebo cushioning component and/or the active cushioning component has been freeze-dried.

As used herein, the phrase "placebo cushioning component" can encompass a bead, particle or granule comprising a highly-compactable filler and a highly water-absorbing material.

The phrase "particle size" refers to the mean diameter of the particles such as, e.g., the placebo cushioning component, the active cushioning component or active-loaded particles as determined by methods such as, e.g., sieving, laser diffraction or optical microscopy.

As used herein, the phrase "pharmaceutical composition" can encompass a designed pharmaceutical formulation assembled (processed) in such a way as to meet certain functional criteria, e.g., appropriate drug release characteristics, stability, manufacturability, patient acceptability, content uniformity.

As used herein, the phrase "loss on drying" when used in connection with freeze drying the placebo cushioning component or freeze-drying the admixture comprising a placebo cushioning component and active-loaded particles means the amount of water remaining in such compositions after completion of freeze-drying.

As used herein, the term "patient" refers to any animal classified as a mammal, including humans, domestic and farm animals, and zoo, sports and pet companion animals such as household pet and other domesticated animals such as, but not limited to, cattle, sheep, ferrets, swine, horses, poultry, rabbits, goats, dogs, cats and the like. Preferred companion animals are dogs and cats. Preferably, the mammal is human.

As used herein, the terms "treat" and "treatment" refer to both therapeutic treatments and prophylactic or preventative measures, wherein the object is to prevent or slow down (lessen) an undesired physiological condition, disorder or disease or obtain beneficial or desired clinical results. For purposes of this invention, beneficial or desired clinical results include but are not limited to, alleviation of symptoms; diminishment of extent of condition, disorder or disease; stabilized (i.e. not worsening) state of condition, disorder or disease; delay or slowing of condition, disorder or disease progression; amelioration of the condition, disorder or disease state; remission (whether partial or total), whether detectable or undetectable; or enhancement or improvement of condition, disorder or disease. Treatment includes eliciting a cellular response that is clinically significant, without excessive levels of side effects. Treatment also includes prolonging survival as compared to expected survival if not receiving treatment.

As used herein, the phrase "biological property" means an in vivo effector or antigenic function or activity that is directly or indirectly performed by a compound of this invention that are often shown by in vitro assays.

As used herein, the phrase "effector function" includes receptor or ligand binding, any enzyme activity or enzyme modulatory activity, any carrier binding activity, any hormonal activity, any activity in promoting or inhibiting adhesion of cells to an extracellular matrix or cell surface molecules, or any structural role.

As used herein, the phrase "antigenic function" includes possession of an epitope or antigenic site that is capable of reacting with antibodies raised against it.

As used herein, the phrases "active agent" and "active pharmaceutical ingredient" can encompass the biologically active ingredient in any pharmaceutical composition that creates the desired biological property in the patient in need of treatment.

As used herein, the phrase "pharmaceutically acceptable salt" includes salts of compounds derived from the combination of a compound and an organic or inorganic acid. These compounds are useful in both free base and salt form. In practice, the use of the salt form amounts to use of the base form; both acid and base addition salts are within the scope of the present invention.

As used herein, the phrase "fast-disintegrating tablet" encompasses a tablet having a disintegration time on the tongue without the addition of liquid beyond that normally available in the mouth due to salivation of between 0-60 seconds with the most preferred disintegration time of 0-20 seconds.

As used herein, the phrase "active-loaded particle" encompasses any active pharmaceutical ingredient.

The phrase "coated active-loaded particle" encompasses an active-loaded particle that is coated with an appropriate coating to achieve a desired result such as enteric, sustained release or taste-masking.

As used herein, the phrase "tablet hardness" refers to a measure of the physical strength of a tablet or the breaking force of a tablet.

As used herein, the term "friability" refers to the ability of the solid dosage forms to resist fracture, chipping and abrasion.

As used herein, the term "cachet" encompasses a dosage form made by enclosing medicinal powder mixtures between two convexly-shaped wafer which disintegrate in the mouth.

As used herein, the term "caplet" encompasses a capsule-shaped tablet.

As used herein, the term "sachet" encompasses a dosage form made by enclosing medicinal powder into a container which disintegrates or dissolves in a liquid.

5.2 The Active Cushioning Component and Methods for Making Thereof

The present invention relates to a compressible dosage form comprising an active cushioning component, wherein the active cushioning component comprises an active agent, a highly-compactable filler and a highly water-absorbing material; and methods for making thereof. This active cushioning component can be made using conventional and scaleable pharmaceutical equipment In one embodiment, the present invention relates to a compressible dosage form comprising an active cushioning component, wherein the active cushioning component comprises:

(a) a placebo cushioning component comprising a highly-compactable filler, a highly water-absorbing material and water; and (b) active-loaded particles; wherein the placebo cushioning component and active-loaded particles are admixed to form an admixture; and the admixture is freeze-dried to form the active cushioning component.

Applicants unexpectedly found that when a placebo cushioning component and moistened active-loaded particles are co-processed and freeze-dried, the resultant active cushioning component comprises non-segregatable, uniformly distributed, active-loaded particles within a layer of cushioning material; and the active-loaded particles exhibit substantially no fracturing or degradation of the active-loaded particles.

In another embodiment, the present invention relates to a compressible dosage form comprising an active cushioning component, wherein the active cushioning component comprises:

(a) a freeze-dried placebo cushioning component comprising a highly-compactable filler and a highly water-absorbing material, and having a particle size ranging from about 20 µm up to about 2000 µm; and (b) active-loaded particles; wherein the freeze-dried placebo cushioning component and active-loaded particles are admixed to form the active cushioning component.

A placebo cushioning component comprising a highly-compactable filler, a highly water-absorbing material and water useful in the present invention is described in U.S. Pat. No. 5,780,055 to Habib et al., the entire contents of which are incorporated herein by reference.

Non-limiting examples of useful highly-compactable fillers include microcrystalline cellulose; compressible forms of lactose such as physically-modified (spray-dried) lactose such as Fast-Flo® Lactose, available from Foremost Ingredient Group, Baraboo, Wis., and anhydrous lactose; unmilled dicalcium phosphate dihydrate; anhydrous dicalcium phosphate; and any combination thereof. In one embodiment, the highly-compactable filler is microcrystalline cellulose.

Non-limiting examples of useful highly water-absorbing materials include internally cross-linked forms of sodium carboxymethylcellulose (croscarmellose sodium), such as Ac-Di-Sol®, available from FMC Corporation, Philadelphia, Pa.; disintegrants and superdisintegrants such as starch, crospovidone and sodium starch glycolate; or hydrophilic materials such as, e.g., hydroxypropyl cellulose.

The amount of highly-compactable filler typically can range from about 5% to about 90% by weight based on the total weight of highly-compactable filler and highly water-absorbable materials. In one embodiment, the amount of highly-compactable filler ranges from about 5% to about 80% by weight based on the total weight of highly-compactable filler and highly water-absorbable materials. And in another embodiment, the amount of highly-compactable filler ranges from about 5% to about 60% by weight based on the total weight of highly-compactable filler and highly water-absorbable materials.

The highly water-absorbing material is present in an amount sufficient to provide the required rate of disintegration of the active cushioning component. In one embodiment, the highly water-absorbing material is present in an amount ranging from about 0.1% up to about 80% based on the weight of highly-compactable filler. In another embodiment, the highly water-absorbing material is present in an amount ranging from about 5% up to about 40% based on the weight of highly-compactable filler. In another embodiment, the highly water-absorbing material is present in an amount ranging from about 20% up to about 40% based on the weight of highly-compactable filler.

The amount of water is that amount sufficient to provide a granular form of the placebo cushioning component during the granulation process. In one embodiment, the amount of water ranges from about 20% to about 80% based on the total weight of highly-compactable filler, highly water-absorbing materials and water; in another embodiment, the amount of water ranges from about 30% to about 60% based on the total weight of highly-compactable filler and water; and in another embodiment, the amount of water ranges from about 40% to about 50% based on the total weight of highly-compactable filler and water.

The cushioning component may further comprise a disintegrant. The disintegrant may be the same or different from the highly water-absorbing material.

Non-limiting examples of useful disintegrants include croscarmellose sodium, sodium starch glycolate, crospovidone, starch, and pregelatinized starch. In one embodiment, the disintegrant is croscarmellose sodium.

When a disintegrant is used, the disintegrant is present in an amount ranging from about 01.% up to about to about 80% based on the weight of highly-compactable filler; in another embodiment, in an amount ranging from about 5% up to about 40% based on the weight of highly-compactable filler; and in another embodiment, in an amount ranging from about 20% up to about 40% based on the weight of highly-compactable filler.

The cushioning component can further comprise a viscosity enhancer. Non-limiting examples of viscosity enhancers include carbomer; xanthan gum; guar gum; alginate; dextran; pectin; pregelatinized starch; polysaccharide; and cellulose derivatives such as hydroxypropyl cellulose, hydroxypropylmethyl cellulose and the sodium, potassium, or calcium salts of carboxymethylcellulose; and combinations thereof.

In one embodiment, the viscosity enhancer is carbomer.

The viscosity enhancer is useful for providing a homogenous suspension when the tablets come in contact with water. Without being limited by theory, Applicants believe that on contact with water, the tablet disintegrates, and the viscosity enhancer swells, resulting in a homogenous suspension consisting of active-loaded particles.

When a viscosity enhancer is used, it is present in an amount sufficient to provide a viscosity that substantially delays sedimentation or precipitation of the active-loaded particle. In one embodiment, the viscosity enhancer is present in an amount sufficient to achieve an apparent viscosity of about 30 to about 3000 mPa·s at 20° C.; in another embodiment, the viscosity enhancer is present in an amount sufficient to achieve an apparent viscosity of about 500 to about 1000 mPa·s at 20° C.

In one embodiment, the viscosity enhancer, when used, is present in an amount ranging from about 0.1% up to about 1% by weight, based on the weight of total weight of the active cushioning component; in another embodiment, the viscosity enhancer, when used, is present in an amount ranging from about 0.1% up to about 0.3% by weight, based on the weight of total weight of the active cushioning component.

The cushioning component may further comprise a filler. Non-limiting examples of useful fillers include e.g., lactose and sorbitol and those fillers described in Section 5.4. In one embodiment, the filler is lactose or sorbitol.

When a filler is present, the amount of filler ranges from about 0.1% to about 80% based on the weight of the cushioning component; in another embodiment, from about 1% to about 60% based on the weight of the cushioning component; and in another embodiment, from about 10% to about 50% based on the weight of the cushioning component.

The placebo cushioning component may further comprise additional excipients such as, e.g., flavorants, sweeteners and colorants as discussed below for the active-loaded particles.

The placebo cushioning component is present in an amount that is sufficient to substantially reduce or eliminate fracturing or degradation of the active-loaded particles during compression. In one embodiment, the amount of placebo cushioning component ranges from about 0.1% up to about 99.9% based on the weight of the active cushioning component; in another embodiment, from about 20% to about 90% based on the weight of the active cushioning component; and in another embodiment, from about 40% to about 75% by weight based on the weight of the active cushioning component.

The placebo cushioning component is of a size that is sufficient to provide a cushioning layer on the drug bead that substantially reduces or eliminates fracturing of the drug bead coating during a compression process. In one embodiment, the particle size of the placebo cushioning component ranges from about 20 μm to about 2000 μm; in another embodiment, the particle size of the placebo cushioning component ranges from about 20 μm to about 1000 μm; and in another embodiment, the particle size of the placebo cushioning component ranges from about 20 μm to about 500 μm.

The amount of active-loaded particles is that sufficient to achieve the desired pharmacological effect and will be determined by factors such as, e.g., tablet size, patient age, type of active agent, concentration of active agent in the active bead and the severity of the condition being treated or prevented. Thus, one of ordinary skill in the art can determine the amount of active bead to be used by routine experimentation. In one embodiment, the amount of active-loaded particle ranges from about 0.1% up to about 99.9% by weight based on the weight of the active cushioning component. In another embodiment, the amount of active-loaded particle ranges from about 1% up to about 80% by weight based on the weight of the active cushioning component. In another embodiment, the amount of active-loaded particle ranges from about 5% up to about 60% by weight based on the weight of the active cushioning component. Methods for making active-loaded bead are described in Section 5.3.

The present invention also relates to methods for making compressible dosage forms comprising an active cushioning component, wherein the active cushioning component comprises an active agent, a highly-compactable filler and a highly water-absorbing material.

In one embodiment, the present invention relates to methods for preparing a compressible dosage form comprising an active cushioning component, comprising:

(a) combining a highly-compactable filler, a highly water-absorbing material and water to form a placebo cushioning component;

(b) providing active-loaded particles;

(c) admixing the placebo cushioning component and active-loaded particles to form an admixture; and (d) freeze-drying the admixture to form the active cushioning component.

Methods for admixing include dry blending, optionally with a binder; wet blending in the form of a mud or suspension mixing, optionally with a binder; extrusion and combinations thereof.

In another embodiment, the present invention relates to methods for preparing a compressible dosage form comprising an active cushioning component, comprising:

(a) combining a highly-compactable filler, a highly water-absorbing material and water to form a placebo cushioning component;

(b) freeze-drying the placebo cushioning component to form a freeze-dried placebo cushioning component;

(c) milling the freeze-dried placebo cushioning component to form a freeze-dried placebo cushioning component having a particle size ranging from about 20 μm up to about 2000 μm;

(d) providing active-loaded particles; and (e) admixing the freeze-dried placebo cushioning component having a particle size ranging from about 20 μm up to about 2000 μm and the active-loaded particles to form the active cushioning component.

The step of forming the placebo cushioning component can be performed, for example, using methods for granulating which are known in the art (see E. M. Rudnic et al. in 45 *Remington's: The Science and Practice of Pharmacy* 868-869 (Alfonso R. Gennaro ed. 2000), the contents of which are incorporated herein by reference). For example, a non-limiting method for forming a placebo cushioning component is disclosed in U.S. Pat. No. 5,780,055 to Habib et al., the entire contents of which are expressly incorporated herein by reference. In one embodiment, the highly-compactable filler and the highly water-absorbing material are admixed to form a dry-blend; and the dry blend is granulated using purified water as the granulating fluid. A non-limiting granulation process useful in the present invention comprises a low-shear wet granulation process using a planetary mixer. The endpoint of granulation of the cushioning components is reached when visual inspection confirms that granules are produced.

The freeze-drying creates the unexpected cushioning characteristic of the active cushioning component (e.g., particles, beads or pellets) and produces a very porous layer of cushioning component that surrounds the active-loaded particles. Protected by the high porosity cushioning component layer, the coatings of the active-loaded particles can withstand a compression force during the tabletting process as high as 1000 kg or more, depending on the nature of the coated active-loaded particle and the proportion, particle size and composition of the compressible active agent particles in the tabletting mixture. In addition to the cushioning characteristic, the freeze-drying creates a non-hygroscopic active cushioning component that does not require any special handling or packaging, thereby reducing costs associated with the use of the existing technology.

The freeze-drying of the placebo cushioning component or the admixture comprising the placebo cushioning component and active-loaded particles can be performed by methods known in the art (see U.S. Pat. No. 5,780,055). A non-limiting method comprises placing the placebo cushioning component or the admixture comprising the placebo cushioning component and active-loaded particles into a freeze-dryer until the desired loss on drying ("LOD") of less than is achieved. For example, freeze-drying can be performed using a Dura-Top® FTS (FTS Systems, Inc. Stone Ridge, N.Y.). A non-limiting example of a freeze-drying process is the staged process shown below in Table 1, where a programmable temperature ramp is employed while maintaining the system under sufficient vacuum to remove the volatile components.

TABLE 1

| Staged freeze-drying process. | | |
|---|---|---|
| Freezing Stage | | Freezing at −20° C. for 2 h |
| Primary Drying | Stage I | Temperature = −20° C.<br>Vacuum = 10 mTorr<br>Time = 700 m |
| | Stage II | Temperature = 0° C.<br>Vacuum = 10 mTorr<br>Time = 600 m |
| Secondary Drying | Stage III | Temperature = 25° C.<br>Vacuum = 10 mTorr<br>Time = 500 m |
| | Stage IV | Temperature = 25° C.<br>Vacuum = atmospheric<br>pressure until end of run |

In one embodiment, the freeze-drying is performed until the placebo cushioning component has an amount of water ranging from about from about 0% up to about 20% based on the total weight of water and other components of the freeze-dried placebo cushioning component. In another embodiment, the freeze-drying is performed until the placebo cushioning component has an amount of water ranging from about from about 2% up to about 15% based on the total weight of water and other components of the freeze-dried placebo cushioning component. In another embodiment, the freeze-drying is performed until the placebo cushioning component has an amount of water ranging from about from about 2% up to about 10% based on the total weight of water and other components of the freeze-dried placebo cushioning component.

In certain embodiments, the admixture comprising the placebo cushioning component and active-loaded particles are passed through a sieve screen of appropriate size as described below.

In certain embodiments, the admixture is extruded. Optionally, the extrudate is spheronized.

Methods of extrusion are known in the art. A non-limiting method of extrusion can be carried out using a LUWA® single-screw extruder through a 1.0 mm screen (Model EXKS-1, LCI Corporation, Charlotte, N.C.) at a speed equivalent to 48 RPM. Extrudate is charged onto a rotating plate and broken into short segments by contact with a friction plate, by collision between particles, and by collisions with the wall. Mechanical energy introduced by the spinning friction plate is transmitted into kinetic energy in the form of a "mechanically fluidized bed", a more-or-less random mixture of air-borne particles moving at high velocities. Further processing causes the extrudate to deform gradually into a spherical shape.

Methods of spheronization are known in the art (see E. M. Rudnic et al. in 45 *Remington's: The Science and Practice of Pharmacy* 870-871 (Alfonso R. Gennaro ed. 2000)), and spheronizers are commercially available from Niro-Aeromatic, Inc. Caleva, LUWA (Fuji Paudal), Machine Collete, Glatt Air Techniques and Patterson Kelley. A spheronizers is a device consisting of a vertical hollow cylinder (bowl) with a horizontal rotating disc (friction plate) located inside. For example, a non-limiting method of spheronization can be carried out using a G.B. Caleva® spheronizer (G.B. Caleva Ltd., Ascot, England) for 5 min at a dial reading of 12.

Upon achievement of the desired size, the active cushioning component can be placed through a sieve to remove fines, milled until a desired particle size is achieved, or moved directly to the tabletting process.

The freeze-dried placebo cushioning component or the freeze-dried admixture comprising the placebo cushioning component and active-loaded particle may optionally be milled until a desired particle size is achieved. Methods of milling are known in the art and include, but are not limited to roller mills, hammer mills, centrifugal-impact mills, cutter mills, attrition mills, chaser mills and ball mills (see R. E. Connor in 37 *Remington's: The Science and Practice of Pharmacy* 681-685 (Alfonso R. Gennaro ed. 2000), the contents of which are incorporated herein be reference). In one embodiment, the milling step is performed until the active cushioning component has a diameter ranging from about 635-10 mesh (20-2000 micron). In another embodiment, the milling step is performed until the active cushioning component has a diameter ranging from about 635-20 mesh (20-850 micron). And in another embodiment, the milling step is performed until the active cushioning component has a diameter ranging from about mesh of 635-40 (20-425 micron).

Without being limited by theory, Applicants believe that the milling step increases the surface area of the freeze-dried placebo cushioning component or the freeze-dried admixture comprising the placebo cushioning component and active-loaded particle and allows a tablet formed from such milled components to rapidly disperse on the tongue without the addition of a liquid beyond the saliva normally in the mouth.

Applicants unexpectedly found that the milled particles readily flow without the need of a lubricant. Such flowability allows the milled particles to be used in dosage forms requiring a finely-divided solid such as, e.g., a cachet.

In certain embodiments, the milling step further comprises a particle size classification step such as, e.g., screening or sieving. Methods of sieving are known in the art. In general, one or more sieve trays of a desired opening are provided, and the trays are arranged so that the size of the screen openings decrease from the top (loading) screen to the lower screens. The milled composition is added to the top screen, the milled composition is shaken or agitated for a time sufficient to separate the milled particles according to size, and the classified particles are removed from the individual trays. Sieves trays are available, e.g., from Newark Wire Cloth Company, Verona, N.J.

5.3 The Active-Loaded Particle

The active-loaded particles comprise one or more active agents and include those active-loaded particles known in the art. Non-limiting examples of active agents useful in the present invention include, e.g., alpha-blockers including, but not limited to, doxazosin, or doxazosin mesylate; angiotension converting enzyme (ACE) inhibitors including, but not limited to, quinapril, or quinapril hydrochloride; angiotension receptor blocker (ARB) including, but not limited to, losartan, or losartan potassium; analgesics; anthelmintics; anti-AIDS agents; anti-angiogenic agents; anti-allergic agents; anti-Alzheimer's disease agents including, but not limited to, donepezil, or donepezil hydrochloride; anti-anginal agents; anti-anaphylaxis therapy agents; anti-anxiety agents including, but not limited to, clonazepam; anti-arrhythmic agents; anti-arthritic agents; anti-asthmatic agents; antibiotics; anticancer agents; anticholinergics; anticoagulants; anticonvulsants; antidepressants; antidiabetic agents including, but not limited to, glipizide; anti-diarrhea agents; antidompaminergics; antiemetics; antiepileptics; antifungals; anti-gout agents; antihistamines including, but not limited to, doxylamine, or doxylamine succinate; antihyperlipidemics; antihypertensive agents; anti-inflammatory agents; antimigraine agents; antimuscarinic agents; antimyasthenic agents; antimycobacterial agents; antineoplastic agents; anti-obesity agents; anti-osteoporosis agents including, but not limited to, risedronate, or risedronate sodium; anti-Parkinson's disease agents including, but not limited to, pramipexole, or pramipexole dihydrochloride; antipyretics including, but not limited to, acetaminophen; anti-psychotics including, but not limited to, olanzapine; anti-rheumatic agents; antispasmodics; antithyroid agents; antiviral agents; antitussives; anxiolytic sedatives; astringents; barbiturates including, but not limited to, phenobarbital; beta-adrenoceptor blocking agents; beta-blockers including, but not limited to, metoprolol, or metoprolol tartrate; calcitonin; cardiotonic agents; catechol-0-methyl transferase (COMT) inhibitors; calcium channel blockers including, but not limited to, amlodipine, or amlodipine besylate; central nervous system (CNS) stimulants including, but not limited to, methylphenidate, amphetamines cholesterol reducing agents including, but not limited to, atorvastatin; cholinesterase inhibitors; contrast media; corticosteroids; cough suppressants including, but not limited to, dextromethorphan, or dextromethorphan hydrobromide; COX-2 inhibitors including, but not limited to, celecoxib; diagnostic agents; diagnostic imaging agents; diuretics including, but not limited to, hydrochlorthiazide; dopaminergics; dopamine receptor antagonists; expectorants; H-2 antagonists; 5HT3 antagonists; haemostatics; hormonal modulating agents; hypnotics; immunomodulating agents; immunosuppressants; interleukin receptor antagonists; laxatives; lipid regulating agents; leukotriene modulators; monoamine oxidase inhibitors (MAOI) including, but not limited to, tranylcypromine, or tranylcypromine sulfate; muscle relaxants; nasal decongestants including, but not limited to, pseudoephedrine, or pseudoephedrine hydrochloride; non-steroidal anti-inflammatory (NSAID) agents including, but not limited to, ibuprofen; opiate analgesics including, but not limited to, morphine, or morphine sulfate; oxytocics; parasympathomimetics; parathyroid; phosphodiesterase enzyme (PDE) inhibitors including, but not limited to, sildenafil; potassium channel blockers; protease inhibitors; proton pump inhibitors (PPIs) including, but not limited to, pantoprazole, or pantoprazole sodium sesquihydrate; prostaglandins; radio-pharmaceuticals; selective serotonin reuptake inhibitor (SSRI) including, but not limited to, sertraline, or sertraline hydrochloride; sex hormones; sodium channel blockers; stimulants; sympathomimetics; thyroid agents; tricyclic antidepressants including, but not limited to, clomipramine, or clomipramine hydrochloride vasodilators and xanthines; any pharmaceutically acceptable salts thereof, and mixtures thereof. Other examples of specific active agents useful in the present invention can be found in *Physicians' Desk Reference* (2000), the entire contents of which are incorporated herein by reference.

Non-limiting examples of active agents useful in the present invention also include dietary supplements such as, e.g., electrolytes such as potassium, calcium and magnesium; vitamins, minerals such as iron and chromium; and amino acids.

Non-limiting examples of active agents useful in the present invention also include steroids including, but not limited to, prednisolone, or prednisolone sodium phosphate; any pharmaceutically acceptable salts thereof, and mixtures thereof.

This invention also encompasses prodrugs or prodrug derivatives of the compounds contained herein. The term "prodrug" refers to a pharmacologically inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo, when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see Bundgard, *Design of Prodrugs* 7-9 and 21-24 (1985) and Silverman, *The Organic Chemistry of Drug Design and Drug Action* 352-401 (1992)). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability. The preparation of pharmaceutically acceptable isomers, solvates or hydrates would be apparent to one of ordinary skill in the art.

The active bead may further comprise one or more inactive ingredients such as binders, disintegrants, fillers (diluents), flavorants, lubricants, glidants depending on the amount and type of active agent, the desired release rate of the drug, and the method of manufacture (see 1 *Pharmaceutical Dosage Forms: Tablets* 75-246 (H. A. Lieberman et al. eds. 1989)). For example, active-loaded particles prepared by an extrusion/spheronization process will typically have the active ingredients distributed throughout the matrix of inactive pharmaceutical excipients such as microcrystalline cellulose in combination with lactose, starch and other appropriate pharmaceutical excipients.

The active-loaded particles are of a shape and size sufficient to form a solid with a suitable content and with suitable release properties including, e.g., spheroid, pellet, cubic or oblong. In one embodiment, the active-loaded particle is a spheroid or a pellet. In another embodiment, the active-loaded particle is a spheroid.

In one embodiment, the particle size of the active-loaded particles range from about 20 µm up to about 2000 µm; in another embodiment, the particle size of the active-loaded particles range from about 20 µm up to about 850 µm; and in another embodiment, the particle size of the active-loaded particles range from about 20 µm to about 600 µm. Methods for making active-loaded particles are of a specific include, e.g., milling and, optionally sieving, as described above.

Figure 1:
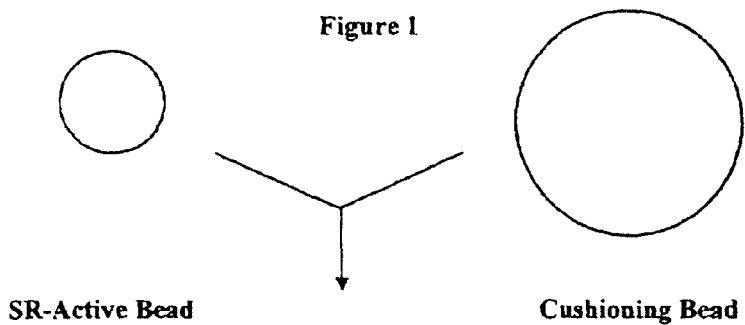
FIG. 1 is shows a cross section of the active cushioning component of the invention prepared from a sustained-release ("SR") active-loaded particle and a placebo cushioning component.
Figure 1:
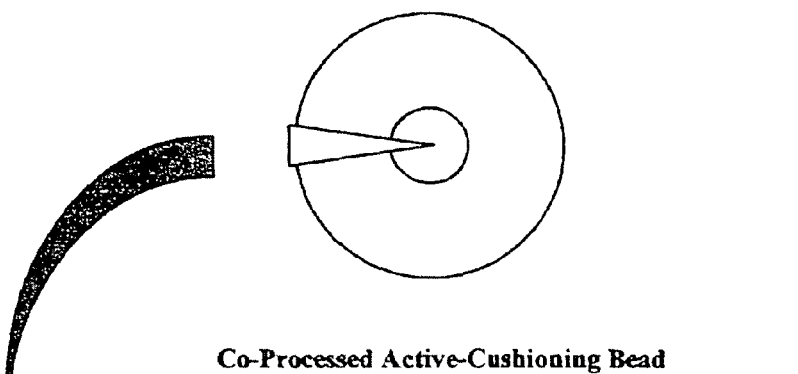
Figure 1:
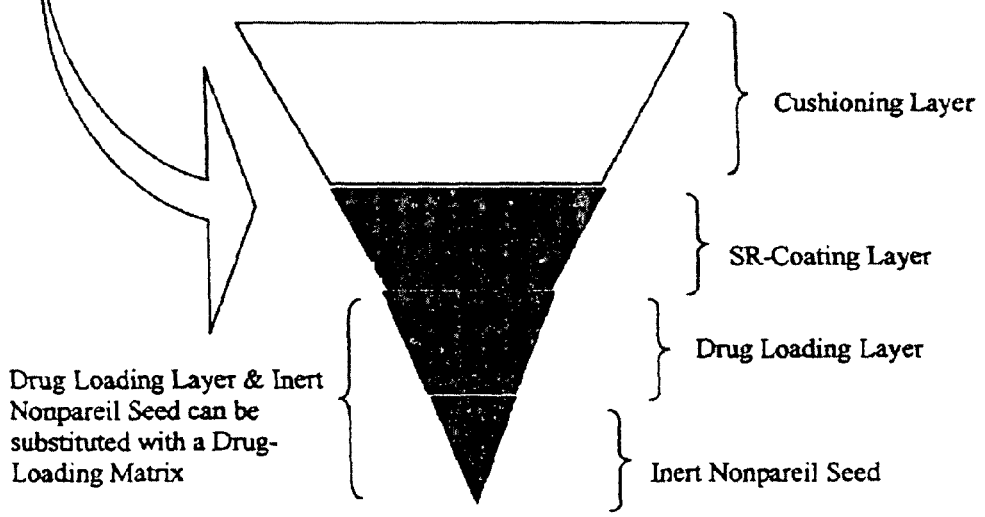

In one embodiment, the active-loaded particle is formed in layers. Active-loaded particles formed by a layering process will typically have the active ingredients deposited around an inert nonpareil seed. The cushioning component then forms a cushioning layer around the active-loaded particles during a subsequent compression process. A cross-sectional view of such active cushioning component is shown in FIG. 1. Here, the active ingredients are dispersed in a binder solution that can be layered onto the nonpareil seeds using a typical fluid-bed coater. A non-limiting example of a suitable binder solution comprises low-viscosity hydroxypropyl-methylcellulose.

In certain embodiments, the active-loaded particles are further coated with a coating comprising one or more functional or non-functional polymers to achieve a desired delivery, e.g., sustained-release, controlled-release, enteric delivery or combinations thereof (see J. W. McGinity, *Aqueous Polymeric Coatings for Pharmaceutical Dosage Forms* (1988).

The type and amount of polymer will depend upon the desired release profile. Non-limiting examples of polymers useful for sustained release coating include cellulosic polymers, such as Aquacoat®, available from FMC Corporation, Philadelphia, Pa., and Surelease®, available from Colorcon, Westpoint, Pa.; and methacrylate ester copolymers such as Eudragit® NE and Eudragit® RS/RL, available from Röhm GmbH and Co., Darmstadt, Del. For enteric release, an enteric coating is used to prevent the contact of the biologically active ingredients with gastric juice and to facilitate the release of the drug in the small intestine region of the GI tract. Non-limiting examples of polymers useful for enteric coatings include methyl(methacrylate) polymers such as Eudragit® L and S, available from Röhm GmbH and Co., Darmstadt, Del.; cellulose acetate phthalate polymers such as Aquateric®, available from FMC Corporation, Philadelphia, Pa.; and polyvinylacetate phthalate such as Sureteric®, available from Colorcon, Westpoint, Pa.

The coating may further comprise excipients such as plasticizers, secondary polymers, and water-soluble and water-insoluble additives to achieve a desired dissolution profile.

In one embodiment, the pharmaceutically active compounds may be made suitably palatable by coating or microencapsulation or by use any other formulation technology known in the art.

5.4 Dosage forms Comprising the Active Cushioning Component and Methods for Making Thereof The present invention also relates to pharmaceutical dosage forms comprising the active cushioning components of the invention, and methods for making pharmaceutical dosage forms. The dosage form can be a solid dosage form or a liquid dosage form such as a suspension or solution.

In one embodiment, the present invention relates to a tablet comprising the active cushioning components of the invention.

In another embodiment, the invention relates to a caplet comprising the active cushioning component of the invention.

In another embodiment, the present invention relates to a lozenge comprising the active cushioning components of the invention.

In another embodiment, the invention relates to a capsule comprising the active cushioning component of the invention.

In another embodiment, the invention relates to a cachet comprising the active cushioning component of the invention.

In another embodiment, the invention relates to a sachet comprising the active cushioning component of the invention.

In another embodiment, the present invention relates to a rapidly disintegrating tablet which disperses in a liquid to form a ready-to-use suspension.

In another embodiment, the present invention relates to a rapidly disintegrating lozenge.

In another embodiment, the present invention relates to a rapidly disintegrating tablet which dissolves in a liquid to form a ready-to-use solution.

In another embodiment, the present invention relates to a rapidly disintegrating tablet which partially dissolves in a liquid to form a ready-to-use solution/suspension.

When a dosage form of the invention comprise a liquid, the liquid can be aqueous (i.e., comprising water), non-aqueous, or a mixture thereof. In one embodiment, the liquid is water. In another embodiment, the liquid is a mixture of water and one or more non-aqueous liquids.

The invention also relates to methods for preparing dosage forms comprising the active cushioning components of the invention.

In one embodiment, the invention relates to methods for preparing rapidly-disintegrating dosage forms comprising active cushioning components of the invention.

In another embodiment, the invention relates to methods for a making a tablet comprising the active cushioning component.

An unexpected advantage of the active cushioning components of the present invention is that the integrity of the functional coatings is substantially maintained during compression.

The tablet of the invention has a hardness sufficient to be robust and having reduced friability, while still having acceptable disintegrating properties. The hardness of the tablet can be measured using any suitable mechanized pharmaceutical hardness tester such as those available from laboratory supply houses such as VanKel Technology Group, 13000 Weston Parkway, Cary, N.C. 27513, or from Erweka Instruments, Inc., 56 Quirk Road, Milford, Conn. 06460.

In one embodiment, the mean hardness of the tablet ranges from about 0.5 kp to about 2.5 kp. In another embodiment, the mean hardness of the tablet ranges from about 0.6 kp to about 2.2 kp. In another embodiment, the mean hardness of the tablet ranges from about 0.6 kp to about 2.0 kp.

Friability is determined using test equipment (also known as friabilators) suitable for testing and verifying the resistance of the solid dosage from chipping and abrasion. Suitable test equipment are available from laboratory supply houses as VanKel Technology Group, 13000 Weston Parkway, Cary, N.C. 27513, or from Erweka Instruments, Inc., 56 Quirk Road, Milford, Conn. 06460.

As noted above, the tablet hardness is one factor that affects the disintegration and/or dissolution time of the tablet. In one embodiment, disintegration time of the tablet of the invention ranges from about 5 s to about 35 s. In another embodiment, disintegration time of the tablet of the invention ranges from about 10 s to about 30 s. In another embodiment, the disintegration time of the tablet ranges from about 10 s to about 25 s.

When the dosage form is a tablet, the amount of active-loaded particles ranges from about 0.1% up to about 99.9% by weight based on the weight of the tablet. In another embodiment, the amount of active-loaded particles ranges from about 1% up to about 80% by weight based on the weight of the tablet. In another embodiment, the amount of active-loaded particles ranges from about 5% up to about 60% by weight based on the weight of tablet. In another embodiment, the amount of active-loaded particles ranges from about 10% up to about 50% by weight based on the weight of tablet. Methods for making active-loaded bead are described in Section 5.3.

The tablet of the invention can further comprise pharmaceutically acceptable viscosity enhancers, fillers, flavorants, sweeteners and lubricants (see, e.g., 1-2 *Pharmaceutical Dosage Forms: Tablets* (H. Lieberman et al. eds. 1989) and *Encyclopedia of Pharmaceutical Technology* (J. Swarbrick and J. Boylan, eds., (2002), the contents of both being incorporated herein by reference).

Non-limiting examples of viscosity enhancers include those discussed above in Section 5.2. When a viscosity enhancer is used, it is present in an amount sufficient to provide a viscosity that substantially delays sedimentation or precipitation of the active-loaded particle. In one embodiment, the viscosity enhancer is present in an amount sufficient to achieve an apparent viscosity of about 30 to 3000 mPa·s at 20° C.; in another embodiment, the viscosity enhancer is present in an amount sufficient to achieve an apparent viscosity of about 500-1000 mPa·s at 20° C.

Non-limiting examples of fillers include, e.g., those selected from among the classes of carbohydrates, inorganic calcium salts, celluloses and starches, soluble and insoluble fillers and other substances identified as fillers, filler-binders, direct compression fillers or diluents and described in common formulation texts such as mannitol (Pearlitol® 200SD) and xylitol (Xylisorb® 300).

When a filler is used, it is present in an amount ranging from about 0.1% to about 80% by weight based on the weight of the tablet; in another embodiment, in another embodiment, in an amount ranging from about 5% to about 60% by weight based on the weight of the tablet; and in another embodiment, in an amount ranging from about 20% to about 50% by weight based on the weight of the tablet.

Flavorants include those flavorants typically used in tabletting formulations such as, e.g., synthetic flavor oils and flavoring aromatics and/or natural oils, extracts from plants, leaves, flowers, fruits and so forth and combinations thereof. Flavorants can also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors useful in the present invention include vanilla, citrus oil, including lemon, orange, grape, lime and grapefruit, and fruit essences, including apple, pear, peach, strawberry, raspberry, cherry, plum, pineapple, apricot and the like.

When a flavorant is used, it is present in an amount ranging from about 0.1% to about 10% by weight based on the weight of the tablet; in another embodiment, in an amount ranging from about 0.5% to about 5% by weight based on the weight of the tablet; and in another embodiment, in an amount ranging from about 1% to about 2.5% by weight based on the weight of the tablet.

Sweeteners include those sweeteners commonly used in tabletting formulation such as, e.g., sucrose, dextrose, sorbitol, mannitol, xylitol or any other pharmaceutically acceptable sugar, sugar alcohol, non-nutritive sweetener, or any combination thereof.

When a sweetener is used, it is present in an amount ranging from about 0.1% to about 80% by weight based on the weight of the tablet; in another embodiment, in another embodiment, in an amount ranging from about 1% to about 60% by weight based on the weight of the tablet; and in another embodiment, in an amount ranging from about 10% to about 60% by weight based on the weight of the tablet.

Non-limiting examples of useful lubricants include, e.g., lubricants selected from among the classes of stearates, stearic acid hydrogenated fats, behenates, fumarates, silicas and others substances generally identified as lubricants, glidants and/or antiadherents in standard formulation texts.

When a lubricant is used, it is present in an amount ranging from about 0.1% to about 10% by weight based on the weight of the tablet; in another embodiment, in an amount ranging from about 0.5% to about 5% by weight based on the weight of the tablet; and in another embodiment, in an amount ranging from about 1% to about 2.5% by weight based on the weight of the tablet.

The tabletting formulations can further comprise other excipients such as, e.g., stabilizers; antioxidants; wetting agents; solubilizers; colorants or pigments such as lakes or dyes; disintegrating agents such as, e.g., modified cellulose such as croscarmellose sodium, NF, modified starch such as sodium starch glycolate, NF or cross-link polyvinylpyrrolidone such as crospovidone, NF; and microbial preservatives as may be required for specific purpose.

The compression of the active cushioning components follows a normal tablet compression operation, and the tablets of the invention can advantageously be manufactured and packaged using conventional equipment. Methods for forming tablets are known in the art (see E. M. Rudnic et al. in 45 *Remington's: The Science and Practice of Pharmacy* 858-902 (Alfonso R. Gennaro ed. 2000), the contents of which are incorporated herein be reference). For example, the tablets can be formed using a Manesty D3B tablet press, available from Thomson Engineering Inc., Hoffman Estates, Ill.

The compression of the active cushioning components is performed with a force sufficient to form a tablet having the desired hardness and disintegration profile. Thus, in one embodiment, mean compression force ranges from about 40 kg to about 140 kg. In another embodiment, the mean compression force ranges from about 50 to about 120 kg. In another embodiment, the mean compression force ranges from about 60 to about 110 kg.

An additional advantage of the current invention is that no additional extra-granular ingredient, especially the binder, is required because of the inter-locking mechanism created by the deformation of the cushioning layer during compression. The resultant tablets not only can maintain their mechanical strength but also can disintegrate rapidly upon contact with water in less than 10 seconds depending on the amount of active.

In one embodiment, the freeze-dried cushioning component is milled, and milled freeze-dried cushioning component is admixed with a taste-masked, sustained-release or enterically-coated active followed by compression into a tablet.

Figure 2:
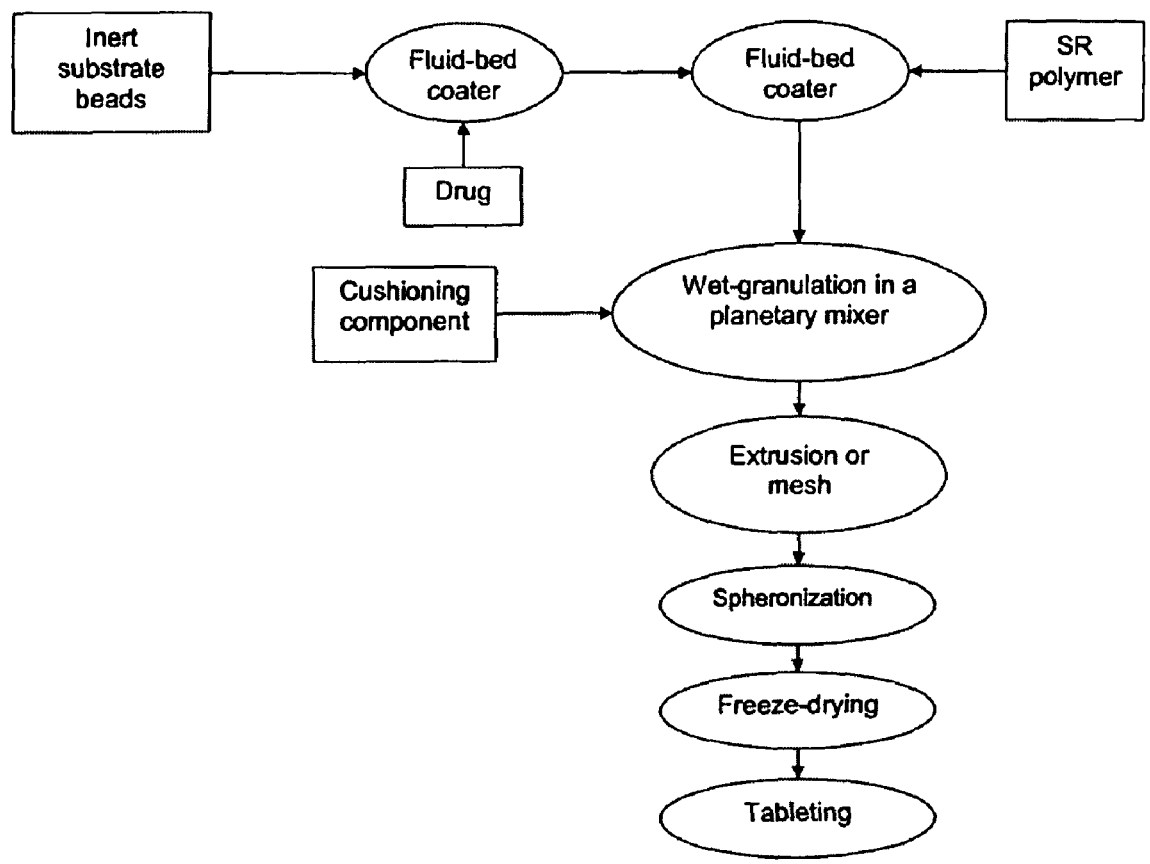
FIG. 2 is a flow-chart showing one embodiment of the invention where a placebo cushioning component was admixed an active-loaded particle to form an admixture; the admixture was freeze-dried to form the active cushioning component; and the active cushioning component was compressed to form a tablet.

FIG. 2 is a flow-chart showing one embodiment of the invention. In this embodiment, an active-loaded particle is coated in a fluidized bed. A placebo cushioning component is admixed with the coated active-loaded particle to form an admixture; the admixture is freeze-dried to form the active cushioning component; and the active cushioning component is compressed to form a tablet.

The invention also relates to methods for forming a cachet comprising the active cushioning component.

In one embodiment, the invention relates to a method for forming a cachet comprising depositing an active cushion component between two wafers, and joining the wafers. The active cushioning component is contained within the cavity formed when the two wafer are joined.

Useful wafers are those that will break apart or disintegrate rapidly in the mount. a useful wafer is rice-flour (see J. B. Sprowls, Jr., *American Pharmacy* 425 (1960)). In one embodiment, the wafer is convexly shaped to provide a "bowl" or cavity for the active cushioning component.

A non-limiting example of a useful wafer comprises rice-flour.

The wafers may be joined by any method known in the art. In one embodiment, the wafers are joined moistening the edges of the wafers prior to joining, and joining the wafers by compressing the edges.

5.5 Methods for Administration

The present invention also relates to methods for administering a dosage form comprising an active cushioning component to a patient in need thereof.

In one embodiment, the dosage forms provides a fast-dissolve on the tongue with the addition of no liquid. beyond that normally available as saliva in the mouth.

In another embodiment, the present invention relates to a method for administering a tablet comprising the active cushioning component of the invention to patient in need thereof.

In another embodiment, the invention relates to a method for administering a capsule comprising the active cushioning component of the invention to patient in need thereof.

In another embodiment, the invention relates to a method for administering a cachet comprising the active cushioning component of the invention to patient in need thereof.

In another embodiment, the invention relates to a method for administering a sachet comprising the active cushioning component of the invention, comprising adding the sachet to a liquid, and administering the resultant suspension or solution to a patient in need thereof.

In another embodiment, the present invention relates to a method for administering a suspension comprising the active cushioning component of the invention and a liquid medium to patient in need thereof.

The precise dose and/or dosage form to be employed will depend on the seriousness of the need of the patient and can be decided according to the judgment of a practitioner and/or each patient's circumstances.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulations or minor changes in experimental design, fall within the scope of the present invention.

6. EXAMPLES

6.1 Example 1

Example 1 describes a non-limiting method for preparing an active cushioning component of the invention, where an admixture comprising a placebo cushioning component and active-loaded particles was freeze-dried and spheronized and compressed into a tablet.

Phase I: Manufacture of Active-Loaded Particles

The manufacture of prednisolone sodium phosphate-loaded beads was carried out by a conventional drug-layering process. The active drug was dissolved in an aqueous dispersion of Opadry® clear, and the resultant dispersion was sprayed onto non-pareil seeds (Celpheres®) on a fluid-bed processor equipped with a Wurster column. The formulation of active drug composition is shown in Table 2.

TABLE 2

| Formulation of Drug-Layering Dispersion | |
|---|---|
| Prednisolone Sodium Phosphate | 12.0% |
| Opadry ® Clear | 2.0% |
| Purified Water | q.s. |

A dispersion of sustained-release coating dispersion was then sprayed onto the active-loaded non-pareil seeds in a manner similar to that described above. The formulation of the sustained-release composition is shown in Table 3.

TABLE 3

| Formulation of Sustained-Release Coating Dispersion. | |
|---|---|
| Eudragit ® NE-30D | 33.3% |
| Talc | 10.0% |
| Purified Water | q.s. |

A dispersion of protective coating dispersion was then sprayed onto the coated active-loaded particles in a manner similar to that described above. The formulation of the protection coating composition is shown in Table 4.

TABLE 4

| Formulation of Protection Coating Dispersion. | |
|---|---|
| Opadry ® II | 12.0% |
| Purified Water | q.s. |

Phase II: Preparation of the Active Cushioning Component

The cushioning materials (see Table 5 below) were dry-blended and then granulated in a planetary mixer via a typical low-shear wet granulation process with purified water as a granulating fluid. Sustained-release coated or enteric coated active-loaded particles were subsequently added to the moistened granules. The moistened granules of the well dispersed, active-loaded particles in the cushioning materials were then passed through a screen of appropriate size and spheronized. The resultant spheroids/bead pellets were then freeze-dried.

TABLE 5

Formulation of Co-Processed Active-loaded particles with Cushioning Beads.

| | |
|---|---|
| Prednisolone Sodium Phosphate SR-coated Beads | 12.0% |
| Microcrystalline Cellulose (Avicel (D PH101) | 61.5% |
| Croscarmellose Sodium (Ac-Di-Sol ®) | 13.5% |
| Purified Water | q.s. |

Manufacturing Procedure:
1. Wet mass the Avicel® PH101 and Ac-Di-Sol® in a low-shear mixer using the Purified Water as granulating fluid until a homogeneous moistened granule mass is obtained
2. Add the Prednisolone Phosphate SR-coated beads to the moistened granule mass in the mixer, and mix until a homogeneous dispersion of active beads is obtained
3. Discharge the moistened granule mass and pass it through a screen with appropriate mesh size. The granule mass is spheronized to produce spheroids/beads.
4. Freeze-dry the spheroids.

Phase III: Compression of the Active Cushioning Component

The final freeze-dried spheroids of the co-processed active-loaded particles with placebo cushioning component were compressed into tablets by hand operating an instrumented Stokes B-2 rotary tablet press. Exemplary disintegration studies of two tablets prepared by the above-described process. Voltages were read off the PC, converted to force using the current calibration curve, and then converted to pressure based on the punch diameter ($^{11}/_{16}$"). The granulation was preweighed and hand-filled into the die. The tablets were made one-at-a-time. The weights reported above represent the actual weights of the finished tablets. The weights and compression pressure used to prepare the tablets are shown below in Table 6.

TABLE 6

Exemplary tablets and control granulations of the present invention. Samples Prepared and Evaluated

| Sample | Weight | Compression Pressure |
|---|---|---|
| Tablet 1 | 1.024 g | 5.6 MPa |
| Tablet 2 | 1.024 g | 10.3 MPa |
| Loose Granulation (Control) | 1.026 g | NA |
| Triturated Granulation | 1.026 g | NA |

Dissolution was carried out using a non-validated UV assay method by means of continuous flow through a 1 cm path length cell using a Van Kel (VK 7000) dissolution system, Van Kel integrated water bath (37°) and Shimadzu UV 160U spectrophotometer fitted with cell changer. The dissolution fluid was 900 mL 0.1N HCl. USP Method 2 (paddles) rotating at 50 RPM was employed. Absorbance was read at 246 nm. every 30 minutes for 12 hours.

Dissolution of the triturated granules (i.e., freeze-dried granules ground to a fine powder using a mortar and pestle) was used as the relative standard; the percent dissolved of the two tablets and the loose granules control were calculated based on the percent dissolved of the tablets or loose (i.e., uncompressed) granules after 12 hours of running vs. the triturated granules. The raw data are provided in Table 7.

TABLE 7

Dissolution Based on Absorbance Readings

| Time (Hrs) | Tablet 1 5.6 MPa | Tablet 2 10.3 MPA | Control | Trituration |
|---|---|---|---|---|
| 0 | 0 | 00.002 | 0 | |
| 0.5 | 0.245 | 0.289 | 0.251 | 0.631 |
| 1 | 0.301 | 0.354 | 0.316 | 0.69 |
| 1.5 | 0.343 | 0.401 | 0.35 | 0.707 |
| 2 | 0.375 | 0.437 | 0.382 | 0.743 |
| 2.5 | 0.404 | 0.467 | 0.406 | 0.761 |
| 3 | 0.429 | 0.493 | 0.43 | 0.778 |
| 3.5 | 0.448 | 0.515 | 0.447 | 0.785 |
| 4 | 0.466 | 0.534 | 0.466 | 0.792 |
| 4.5 | 0.481 | 0.55 | 0.482 | 0.801 |
| 5 | 0.495 | 0.566 | 0.498 | 0.81 |
| 5.5 | 0.509 | 0.581 | 0.512 | 0.819 |
| 6 | 0.523 | 0.594 | 0.528 | 0.824 |
| 6.5 | 0.535 | 0.608 | 0.543 | 0.832 |
| 7 | 0.548 | 0.619 | 0.556 | 0.84 |
| 7.5 | 0.559 | 0.632 | 0.569 | 0.846 |
| 8 | 0.573 | 0.643 | 0.582 | 0.85 |
| 8.5 | 0.583 | 0.655 | 0.596 | 0.857 |
| 9 | 0.594 | 0.665 | 0.607 | 0.862 |
| 9.5 | 0.605 | 0.676 | 0.619 | 0.868 |
| 10 | 0.615 | 0.685 | 0.63 | 0.874 |
| 10.5 | 0.626 | 0.695 | 0.642 | 0.879 |
| 11 | 0.636 | 0.703 | 0.652 | 0.883 |
| 11.5 | 0.644 | 0.712 | 0.663 | 0.887 |
| 12 | 0.653 | 0.721 | 0.675 | 0.892 |

The data from Table 7, after being normalized to the triturated granules, are provided in Table 8 and FIG. 3.

TABLE 8

Calculated % dissolved from a 12 h dissolution relative to triturated granules.

| Time (Hrs) | Tablet 1 (5.6 MPa) | Tablet 2 (10.3 MPa) | Granules (Control) | Triturated granules |
|---|---|---|---|---|
| 0 | 0 | 0.0 | 0.2 | 0.0 |
| 0.5 | 27.5 | 32.4 | 28.1 | 70.7 |
| 1 | 33.7 | 39.7 | 35.4 | 77.4 |
| 1.5 | 38.5 | 45.0 | 39.2 | 79.3 |
| 2 | 42.0 | 49.0 | 42.8 | 83.3 |
| 2.5 | 45.3 | 52.4 | 45.5 | 85.3 |
| 3 | 48.1 | 55.3 | 48.2 | 87.2 |
| 3.5 | 50.2 | 57.7 | 50.1 | 88.0 |
| 4 | 52.2 | 59.9 | 52.2 | 88.8 |
| 4.5 | 53.9 | 61.7 | 54.0 | 89.8 |
| 5 | 55.5 | 63.5 | 55.8 | 90.8 |
| 5.5 | 57.1 | 65.1 | 57.4 | 91.8 |
| 6 | 58.6 | 66.6 | 59.2 | 92.4 |
| 6.5 | 60.0 | 68.2 | 60.9 | 93.3 |
| 7 | 61.4 | 69.4 | 62.3 | 94.2 |
| 7.5 | 62.7 | 70.9 | 63.8 | 94.8 |
| 8 | 64.2 | 72.1 | 65.2 | 95.3 |
| 8.5 | 65.4 | 73.4 | 66.8 | 96.1 |
| 9 | 66.6 | 74.6 | 68.0 | 96.6 |
| 9.5 | 67.8 | 75.8 | 69.4 | 97.3 |
| 10 | 68.9 | 76.8 | 70.6 | 98.0 |
| 10.5 | 70.2 | 77.9 | 72.0 | 98.5 |
| 11 | 71.3 | 78.8 | 73.1 | 99.0 |
| 11.5 | 72.2 | 79.8 | 74.3 | 99.4 |
| 12 | 73.2 | 80.8 | 75.7 | 100.0 |

Similarity metrics (f2) were used to compare the similarity of the Control and Tablets 1 and 2. The results based on comparison at 12 equi-spaced (hourly) time points from 1 to 12 hours are provided in Table 9.

TABLE 9

| Similarity metrics (f2) comparing the similarity of the control and tablets 1 and 2. | |
| --- | --- |
| Comparison | $f_2$ |
| Tab 1 (5.6 MPa) vs. Control | 89.3 |
| Tab 1 (5.6 MPa) vs. Tab 2 (10.3-NIP a) | 55.8 |

These data indicate that the cushioning system is working. The degree of similarity between Tablet 1 (5.6 MPa) and the loose, uncompressed granulation (Control) is extremely high, with an f2 of 89.3. Compression to 10.4 MPa has obviously caused some damage to the SR beads as evidenced by the more rapid. dissolution of the drug from Tablet 2. Nevertheless, using FDA's criterion for similarity, (f2= or >50 indicates similarity), the dissolution profiles of Tablets 1 and 2 would still be considered similar for regulatory purposes.

Tablet 1 and Tablet 2 dissolution profiles (FIG. 3) are quite linear in time in the range from 1 to 12 hours, with correlation coefficients against time of 0.9797 and 0.9733, respectively.

6.2 Example 2

Example 2 describes two non-limiting embodiments of the invention describing how an active-loaded drug bead (Tablet 3) and an uncoated freeze-dried, placebo drug bead (milled and sieved after freeze-drying) (Tablet 4) could be prepared. The formulations of these tablets are provided in Table 10.

TABLE 10

| Tablets formed sing coated and uncoated active-agent beads. | | | |
| --- | --- | --- | --- |
| Components | | Tablet 3: Vitamin C, 250 mg/tablet | Tablet 4: Sodium Phenylbutyrate 400 mg/tablet |
| Drug beads | Coated with up to 5% weight gain with Opadry) | 264 mg | — |
| | Uncoated (80% drug load) | — | 500 mg |
| Milled Freeze-Dried Cushioning Component | Typical size distribution, % greater than: 0.25 mm, 40.3% 0.18 mm, 24.3% 0.10 mm, 16.8% 0.09 mm, 3.7% 0.075 mm, 4.0% <0.075 mm, 10.9% | 80 mg | 400 mg |
| Fillers | Pearlitol 200SD | 60 mg | 90 mg |
| | Xylisorb 300 | 60 mg | — |
| Flavor | Orange Flavor (Firmenich NNA) | 1 mg | — |
| Lubricants | Sodium stearyl fumarate | 5 mg | — |
| | Magnesium stearate | | 10 mg |
| Total tablet weight | | 500 mg | 1000 mg |

Tablet 3 is expected to form an orally disintegrating tablet, i.e., a tablet that rapidly disintegrates in the mouth without need for chewing and eliminates the need to be swallowed whole with a drink of water.

Tablet 4 is expected to form a tablet that rapidly disperses in water to form a drinkable suspension, and, therefore, would allow for the administration of large doses of drug without the need to swallow multiple whole tablets at each dosing interval.

6.3 Example 3

Example 3 describes a non-limiting process for preparing active cushioning components comprising freeze-dried placebos (milled and sieved after freeze-drying), coated active-loaded particles, and excipients. Example 3 also describes non-limiting ranges for each step in the process for placebo tablets and active-loaded tablets.

Tablets 5-10 were prepared as follows:
 i) Freeze-dried beads (prepared as described in U.S. Pat. No. 5,780,055 were milled and sieved through a 35 mesh US Standard screen;
 ii) All excipients and the active-loaded particles in Table 11 were accurately weighed out and passed through a screen;
 iii) All excipients except the lubricant were mixed until uniform in a suitable container;
 iv) The lubricant was added to the blend and the blend was mixed until uniform; and
 v) Tablets weighing about 350 mg were compressed on a Manesty D3B tablet press.

The formulations of the tablets are provided in Table 11.

TABLE 11

| Tablet formulations. | | | | | | |
| --- | --- | --- | --- | --- | --- | --- |
| | Tablet formulation (mg) | | | | | |
| | 5 | 6 | 7 | 8 | 9 | 10 |
| Dextromethorphan Hydrobromide (taste-masked) | | | 72.5 | 72.5 | 36.2 | |
| Ascorbic acid | | | | | | 46.34 |
| Mannitol | 250.3 | 222.3 | 190.9 | 190.9 | 212.1 | 191.33 |
| Xylitol | 63 | 56 | 49 | 49 | 54.25 | 50 |
| Freeze-dried Beads | 35 | 70 | 35 | 35 | 43.75 | 57 |
| Magnesium Stearate | 1.75 | 1.75 | | | | |
| Screen Size (material passing thru the screen was used) | | | #35 | #35 | #40 | #35 |
| Flavoring agent | | | | | 0.875 | 2.5 |
| Sweetener | | | | | 0.175 | 0.33 |
| Sodium Stearyl Fumarate | | | 2.6 | 2.6 | 2.635 | 2.5 |

The hardness and disintegration times of Tablets 6-10, corresponding to Tablet formulations 6-10, respectively, are shown in Table 12.

TABLE 12

| Hardness and disintegrating data for the compressed tablets prepared with different compression force. | | | |
| --- | --- | --- | --- |
| Tablet | Mean Compression Force (kg) | Mean Hardness (kp) | Mean In Vivo Dissolving Time (sec.) |
| 6 | 52.5 | 0.6 | 11.7 |
| | 72.3 | 1.3 | 16.0 |
| | 110.5 | 1.7 | 28.0 |
| 7 | 61.1 | 0.6 | 11.7 |
| | 75.2 | 1.1 | 14.3 |
| | 113.4 | 1.9 | 23.7 |
| 8 | 60.1 | 0.6 | 9.3 |
| | 76.8 | 1.0 | 15.7 |
| | 122.8 | 1.8 | 25.5 |
| 9 | 56.4 | 0.6 | 8.7 |
| | 77.6 | 1.0 | 17.0 |
| 10 | 52.9- | 0.5 | 9.7 |
| | 83.8 | 1.0 | 10.0 |
| | 126.3 | 2.0 | 16.0 |

The disintegration time of the placebo tablet ranged from about 12 s to about 28 s depending on how hard the tablets were compressed. Similarly, the disintegration time of active-loaded tablets 7-10 was about 8-25 seconds, depending on how hard the tablets were compressed.

The results show that tablets of suitable hardness and having suitable disintegration properties can be prepared by compressing active cushioning components comprising a freeze-dried cushioning component and active-loaded particles.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

We claim the following:

1. A compressible dosage form comprising a substantially uniform distribution of active cushioning components, wherein the active cushioning component is a bead, granule, particle or pellet and, wherein the active cushioning component comprises:
  a) a core comprising an active-loaded particle; and
  b) a porous cushioning layer surrounding the core, wherein the cushioning layer comprises a highly compactable filler, and a highly water absorbing material;
wherein the active cushioning component is made by a process comprising
  i) admixing the highly compactable filler, the highly water absorbing material, water and the active-loaded particles to form an admixture and forming a bead, granule, particle or pellet; and
  ii) freeze-drying the bead, granule, particle or pellet to form the active cushioning component, wherein the freeze-drying process creates the porous cushioning layer that surrounds the active-loaded particle core, wherein the active-loaded particles exhibit substantially no fracturing or degradation during compression.

2. The compressible dosage form of claim 1, wherein the cushioning layer of part (b) is a bead or particle and has a particle size ranging from about 20 μm up to about 2000 μm.

3. The compressible dosage form of claim 2, wherein the cushioning layer is a bead or particle and has a particle size ranging from about 20 μm up to about 1000 μm.

4. The compressible dosage form of claim 2, wherein the cushioning layer is a bead or particle and has a particle size ranging from about 20 μm up to about 500 μm.

5. The compressible dosage form of claim 1, wherein the active-loaded particles are present in an amount ranging from about 0.1% to about 97% by weight based on the total weight of the active cushioning component.

6. The compressible dosage form of claim 1, wherein the active-loaded particles are present in an amount ranging from about 20% to about 90% by weight based on the total weight of the active cushioning component.

7. The compressible dosage form of claim 1, wherein the active-loaded particles are present in an amount ranging from about 40% to about 75% by weight based on the total weight of the active cushioning component.

8. The compressible dosage form of claim 1, wherein the highly compactable filler is present in an amount ranging from about 5% to about 90% based on the combined weight of highly-water absorbing material and compactable filler.

9. The compressible dosage form of claim 8, wherein the highly compactable filler is present in an amount ranging from about 5% to about 80% based on the combined weight of highly-water absorbing material and compactable filler.

10. The compressible dosage form of claim 8, wherein the highly compactable filler is present in an amount ranging from about 5% to about 60% based on the combined weight of highly-water absorbing material and compactable filler.

11. A tablet comprising the compressible dosage form of claim 1.

* * * * *